(12) United States Patent
Szkulmowski et al.

(10) Patent No.: US 9,347,880 B2
(45) Date of Patent: May 24, 2016

(54) METHOD AND APPARATUS FOR IMAGING OF SEMI-TRANSPARENT MATTER

(75) Inventors: Maciej Szkulmowski, Torun (PL); Maciej Wojtkowski, Torun (PL); Anna Szkulmowska, Torun (PL); Tomasz Bajraszewski, Glogowo (PL)

(73) Assignee: CANON OPHTHALMIC TECHNOLOGIES SP. Z O.O, Wroclaw (PL)

( * ) Notice: Subject to any disclaimer, the term of this patent is extended or adjusted under 35 U.S.C. 154(b) by 270 days.

(21) Appl. No.: 13/062,025

(22) PCT Filed: Aug. 31, 2009

(86) PCT No.: PCT/EP2009/006294
§ 371 (c)(1),
(2), (4) Date: Mar. 3, 2011

(87) PCT Pub. No.: WO2010/025882
PCT Pub. Date: Mar. 11, 2010

(65) Prior Publication Data
US 2011/0164791 A1    Jul. 7, 2011

(30) Foreign Application Priority Data

Sep. 5, 2008    (EP) ..................................... 08015674

(51) Int. Cl.
| | | |
|---|---|---|
| *G01B 9/02* | (2006.01) | |
| *G01N 21/47* | (2006.01) | |
| *A61B 5/00* | (2006.01) | |
| *A61B 3/10* | (2006.01) | |
| *A61B 3/12* | (2006.01) | |

(52) U.S. Cl.
CPC .......... *G01N 21/4795* (2013.01); *A61B 5/0059* (2013.01); *A61B 5/0066* (2013.01); *G01B 9/02044* (2013.01); *G01B 9/02078* (2013.01); *G01B 9/02091* (2013.01); *A61B 3/102* (2013.01); *A61B 3/1233* (2013.01)

(58) Field of Classification Search
CPC .... A61B 5/0066; A61B 3/102; A61B 5/0073; G01B 9/02091; G01N 21/4795; G01N 2021/1787
USPC .................................................. 356/479, 497
See application file for complete search history.

(56) References Cited

U.S. PATENT DOCUMENTS

| | | | |
|---|---|---|---|
| 5,278,805 A * | 1/1994 | Kimball | 367/32 |
| 7,268,889 B2 * | 9/2007 | Kulawiec et al. | 356/511 |
| 7,336,366 B2 | 2/2008 | Choma et al. | |
| 7,364,296 B2 * | 4/2008 | Miller et al. | 351/206 |

FOREIGN PATENT DOCUMENTS

| | | |
|---|---|---|
| JP | 2010-505127 A | 2/2012 |
| WO | 2008039660 A2 | 4/2008 |

OTHER PUBLICATIONS

Huang et al., "Optical Coherence Tomography," Science, 1991, 254:1178-1181.

(Continued)

*Primary Examiner* — Kara E Geisel
*Assistant Examiner* — Rufus Phillips
(74) *Attorney, Agent, or Firm* — Casimir Jones, S.C.; Mary Ann Brow

(57) ABSTRACT

The invention relates to a method and apparatus for measuring the spatial and velocity distribution of scattering structures of a sample in semi-transparent matter. The acquired spectral data $I(k, t)$ are transformed in two steps to image data $I(z, v)$. A Doppler shift is imposed on the light to a separate real and mirror images in the v space to suppress the complex ambiguity artifact.

14 Claims, 4 Drawing Sheets

(56) References Cited

OTHER PUBLICATIONS

Huber et al., "Amplified, frequency swept lasers for frequency domain reflectormetry and OCT imaging: design and scaling principles," Optics Express, 2005, 13(9):3513-3528.

WO2008039660 is the English language equivalent of JP2010-505127.

Szkulmowski, et al. "Flow velocity estimation using Joint Spectral and Time domain Optical Coherence Tomography" Optics Express Opt. Soc. America USA, vol. 16, No. 9, Apr. 14, 2008, pp. 6008-6025.

* cited by examiner

METHOD AND APPARATUS FOR IMAGING OF SEMI-TRANSPARENT MATTER

This application is a §371 US National Entry of International Application No. PCT/EP2009/006294, filed Aug. 31, 2009, which is incorporated herein by reference and which claims the benefit of European Application No. 08015674.8, filed Sep. 5, 2008.

The invention relates to a method and apparatus for measuring the spatial and velocity distribution of scattering structures of a sample of semi-transparent matter.

Optical coherence tomography (OCT) is a technique for examination of three-dimensional structures of partially transparent matter. According to this technique, low coherent light is divided into two portions. One portion is used as sample light to be passed into a sample path to illuminate the sample under investigation. The second portion is used as reference light and led through a reference path to be recombined at a point of recombination with the light back-scattered from the sample. The recombined light contains an interferometric signal carrying information about the internal structure of the sample. This information can be retrieved in essentially two different ways.

The first way, known as "Time domain Optical Coherence Tomography" (TdOCT), is based on a scannable optical path delay introduced in the reference path. The delay is scanned in an oscillating manner. In this case, interference fringes occur only in certain scan positions, namely in positions in which the optical path length of the reference path matches the optical path length for the light back-scattered by the sample. This facilitates determination of the relative distances of back-scattering structures within the sample (see Huang et al., Science, Vol. 254, 1991, p. 1178 to 1181).

The second way for retrieving information from the recombined light, known as "Fourier domain Optical Coherence Tomography" (FdOCT), is based on spectral analysis of the recombined light. The spectrum of the recombined light, i.e. the distribution of the light intensities for the various spectral components, is recorded. This can be performed by using either a spectrometer ("Spectral Optical Coherence Tomography", SOCT; see Szkulmowska et al., Journal of Physics D: Applied Physics, Vo. 38, 2005, 2606-2611), or a tuned light source ("Swept Source Optical Coherence Tomography", SS-OCT; see R. Huber et al., Optics Express, Vol. 13, 2005, 3513-3528).

Common OCT devices comprise means for scanning the light beam illuminating the eye transversally, i.e. in one or two directions perpendicular to the axis of said light beam. A two- or three-dimensional image of the internal sample structure is thus generated. The axis parallel to the light beam is usually called the z axis and the recordal of the information about the structure along this axis is called "A scan". The other perpendicular axes are called x and y axes. A set of A scans taken along the x axis forms a two-dimensional "xz" tomogram called "B scan", while a set of B scans acquired along the y axis forms a volume data set allowing for formation of "xy" and "yz" tomograms.

In addition to three-dimensional imaging of structures, OCT has proven to be capable of measuring velocities of moving matters inside the structures, e.g. blood flow within tissue samples. Szkulmowski et al., Optics Express, Vol. 16, 2008, 6008-6025, presented a method in which combined TdOCT and SOCT is performed in a single A scan position. A plurality of spectra I(k) are acquired at known time intervals so that a data set I(k, t) is generated. This data set is transformed in two steps into a data set I(z, v) representing the spatial and velocity distribution of the back-scattering structures of the sample, where v represents the velocity components along the axis z of back-scattering structures of the sample. The first step may be a k-z transformation, e.g. Fourier transformation, from the wavenumber domain to the spatial domain yielding a data set I(z, t). In this case, the second step will be a t-v transformation, likewise e.g. Fourier transformation, from the time domain to the velocity domain yielding the desired data set I(z, v). When using Fourier transformation, the transform variable for the time t is the frequency ω, not the velocity v. However, these two parameters ω and v are linked by the relationship ω=2kv, representing the beat frequency resulting from the Doppler shift caused by those back-scattering structures of the sample, which are moving with velocity v.

A general problem associated with SOCT is the complex ambiguity artifact. Because the interference signal is of complex nature, but only real values are detected and processed, the generated image contains the real image and its mirror image rendering the image ambiguous. In order to remove this artifact, it has been proposed to ensure that any back-scattering portion of the sample is placed at positive z values. To this end, the entire sample must be placed apart from the point for which the optical length matches the optical length of the reference path (z=0 position). However, this limits the detection range significantly and requires that the region of this range with the highest sensitivity, namely the range around z=0, be unused.

The object of the invention is to provide a method and an apparatus for measuring the spatial and velocity distribution of scattering structures of a sample of semitransparent matter in which the complex ambiguity artifact is suppressed in the I(z, v) data set while the full spatial detection range is used. This object is achieved by the subject-matter defined in claims 1 and 7. The sub-claims define further improvements.

The invention is based on the idea of separating the real and mirror images with the help of an artificially generated Doppler shift. This may be visualized by FIGS. 1 to 3 of the drawings in which.

Figure 1:
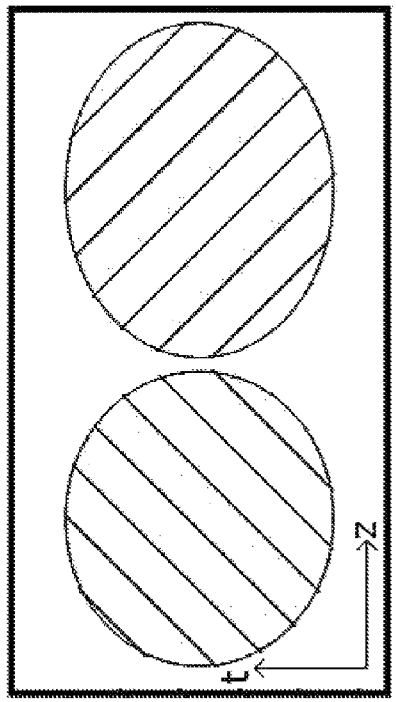
FIGS. 1 and 2 are visualizations of the effects of transformations of an SOCT data set performed according to the prior art.
Figure 1:
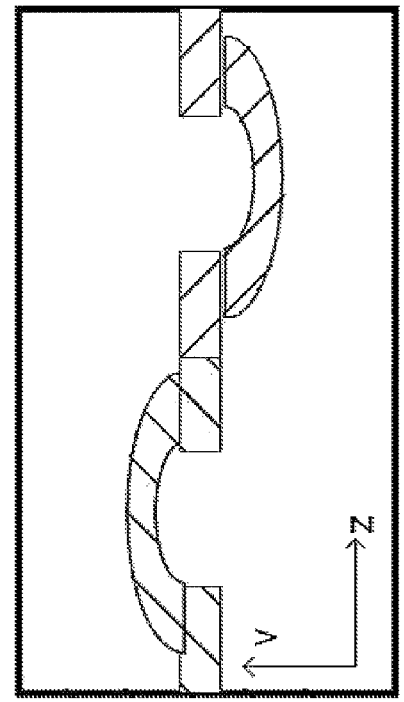
Figure 1:
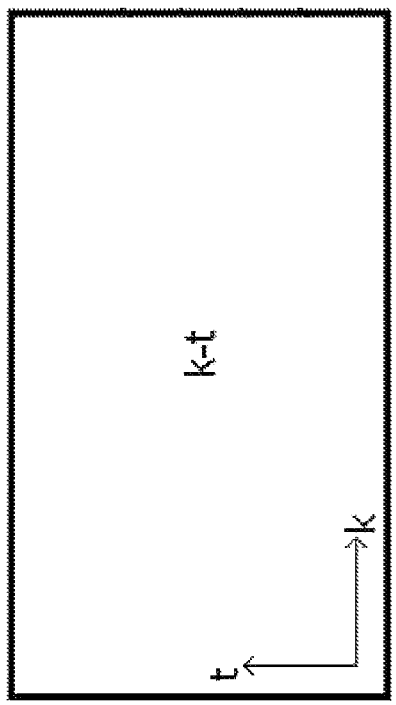
Figure 1:
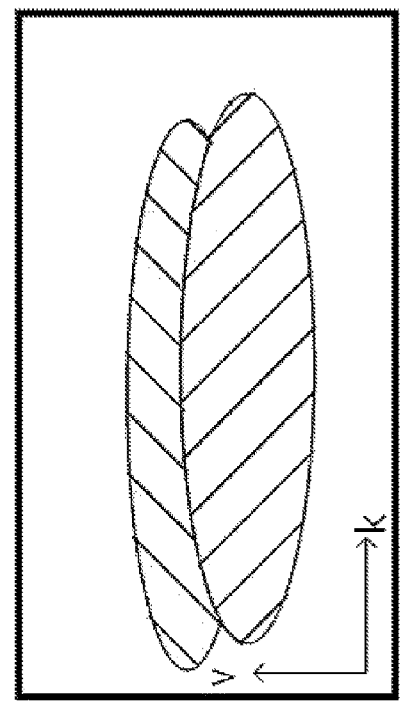

FIG. 1 shows four boxes, each representing a data set. The top left box contains the data set I(k, t) acquired from the SOCT measurements. From here, two transformations are possible. If one performs a k-z transformation first, one arrives at the top right box representing the I(z, t) data set. In contrast, if the t-v transformation is carried out at first, the data set is turned into an I(k, v) data set represented by the bottom left box. In both instances, the second transformation results in the desired I(z, v) data set in the box in the bottom right. This second transformation is the t-v transformation if the k-z transformation had been the first. Mutatis mutandis, the k-z transformation is performed second if the t-v transformation had been carried out first.

The data belonging to the real images within the boxes are marked by hatchings that run from the bottom left to the top right, while the data relating to the mirror images are displayed in hatchings that run from the top left to the bottom right. One can see in FIG. 1 that the k-z transformation separates both portions of data. This is due to the fact that the z=0 position is located outside the sample.

Figure 2:
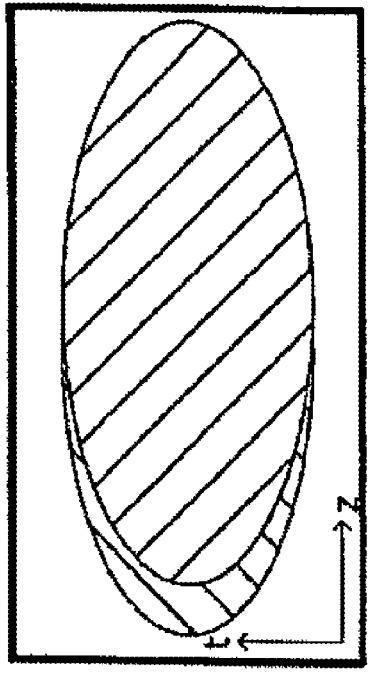
Figure 2:
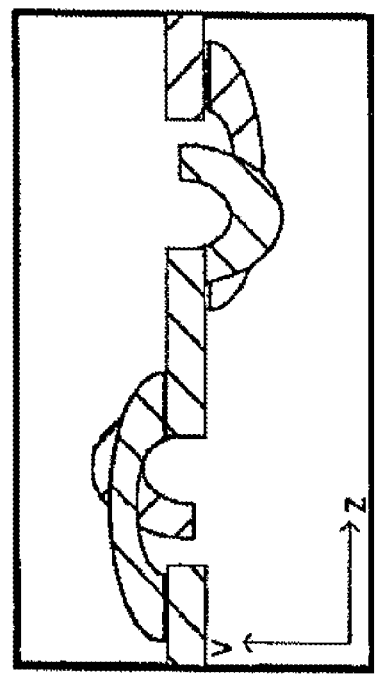
Figure 2:
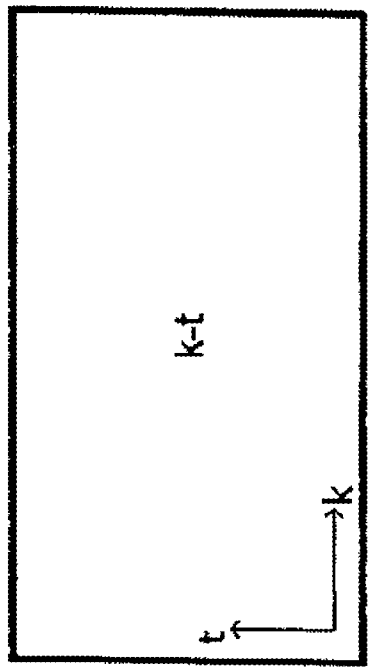
Figure 2:
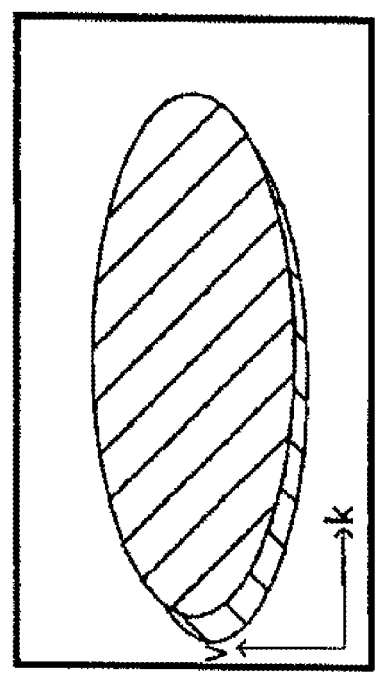
Figure 3:
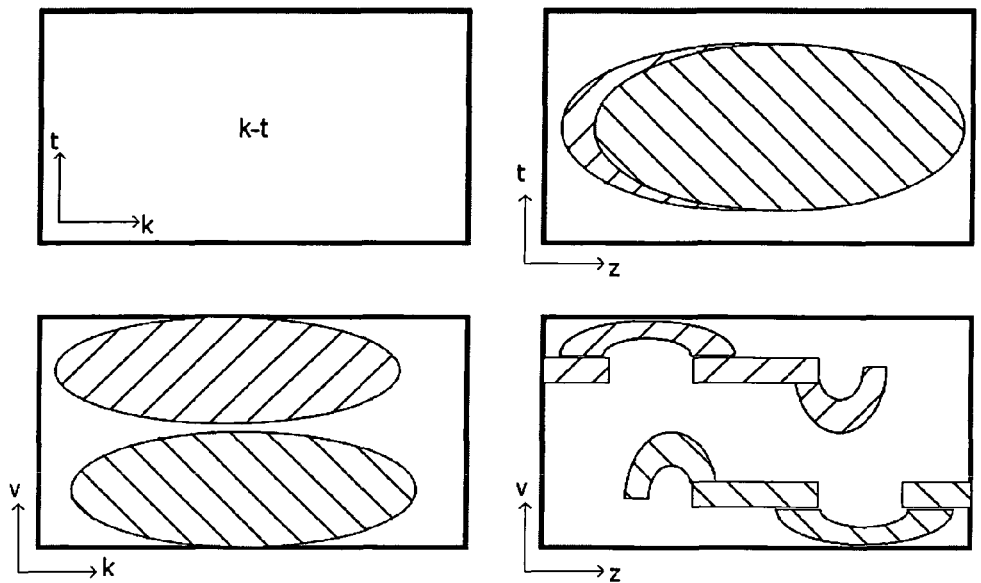
FIGS. 3 and 4 are visualizations of the effects of transformations of an SOCT data set performed according to the invention.

If the latter is not the case, i.e. the z=0 position is located inside the sample, one will find a situation as illustrated in FIG. 2. The portions of data belonging to the real and mirror images overlap which renders the interpretation of the images ambiguous.

The invention is based on the insight that the introduction of an additional, artificially generated Doppler shift in the light causes the data portions belonging to the real and mirror images to shift in opposite directions in the v domain. Such a Doppler shift causes the sample light and the reference light to appear at the point of recombination as originating from sources moving relatively to each other with a velocity $v_D$. $v_D$ is ≠0 and preferably constant during the acquisition of spectra. $v_D$ is defined as an absolute value here, i.e. always $v_D>0$. Where the direction of the imposed Doppler shift varies, the change of algebraic sign +/− must be accounted for in the evaluation. This is, for instance, the case if the Doppler shift is generated with a moving mirror to the driving mechanism of which a triangular control signal is applied and both ramps of the signal are used for the measurement. If the shift is large enough, the data portions will be fully, i.e. with all velocity components v inside the sample, separated so that the complex ambiguity artefact is completely removed. So it is usually preferred to select $v_D$ as large as possible.

However, if the range of detectable velocities within the sample under investigation is known, it is advantageous to limit $v_D$ in order to achieve maximum sensitivity. If the velocities v range between $v_{Min}$ and $v_{Max}$ and $|v_{Min}|=|v_{Max}|$, $V_D$ should be selected to be as closely as possible to $|v_{Max}|$, e.g. between $|v_{Max}|$ and 1.2 $|v_{Max}|$. For many measurements inside the human eye, for instance, v values range between −5 mm/s to 5 mm/s so $v_D$ should be chosen to range between 5 mm/s and 6 mm/s. Higher velocities with absolute values of up to 30 mm/s may be found in the proximity of the optic disc so $v_D$ should be chosen to range between 30 mm/s and 36 mm/s. There are also applications, e.g. measuring blood perfusion of damaged retinal tissue, where v ranges within narrow boundaries, e.g. within the range of −50 μm/s to 50 μm/s, so the invention may be used with $v_D$ within 50 μm/s and 60 μm/s.

If $|v_{Min}|≠|v_{Max}|$, which may occur, for instance, if a vessel under investigation is tilted within a plane parallel to the z axis, $v_D$ may be set as closely as possible to the lower absolute value of $v_{Min}$ and $v_{Max}$ to achieve full separation in the v space. The direction of $v_D$ should be selected accordingly.

Figure 4:
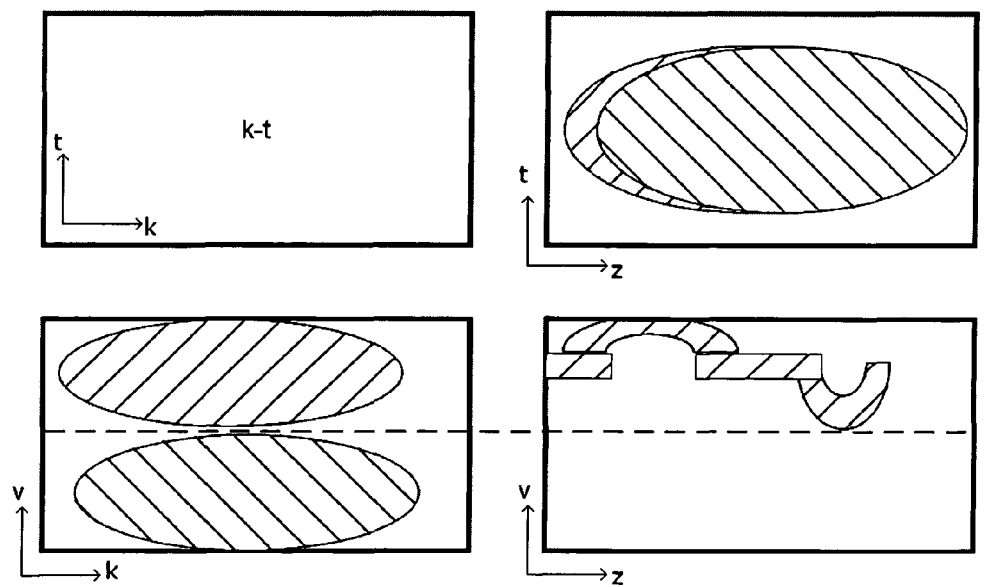

As only one of the real and mirror images is needed, the number of calculation steps can be reduced considerably by using only a portion of the data set I(k, v) for which v is above or below a certain value. This is illustrated in FIG. 4, where the dotted line across both bottom boxes represents said certain value for v. The certain value is preferably be chosen to be the center of the entire range for v of the data set I(k, v).

The Doppler shift is preferably imposed on the reference light as this allows simplified arrangements. It is further advantageous to impose the Doppler shift by using a moving mirror. Using a moving mirror for generating the Doppler shift is particularly advantageous for SOCT as the shift can be introduced without dispersive effects. More preferably, the mirror is arranged perpendicularly to the incident light and moves with velocity $v_D$ along the axis of the incident light. This allows for a simple design and adjustment of $v_D$ by simply changing the velocity of the mirror.

The upper limit for $v_D$ is determined by the range 0 to $v_{DetMax}$ of velocities v which are detectable by the particular SOCT setup. This range of detectable velocities is basically dependent on the lengths of the time intervals between recordings of spectra I(k). In most cases, these intervals are constant and determined by the acquisition speed of the particular detector in use. If Δt is the thus determined time interval, $v_{DetMax}$ will be $\pi/(2k_0\Delta t)$ or, if the influence of different wavelengths shall be accounted for, $\pi/(2k_0\Delta t)$, where $k_0$ is the central wavenumber and $k_{Max}$ is the maximum wavenumber of the spectrum used for the measurement. As in most applications, the distribution of velocities will be centered around v=0, it is advisable to shift this center with the imposed Doppler shift to the center of detectable velocities, i.e., to $v_{DetMax}/2$. It is therefore advantageous to select $v_D$ around $v_{DetMax}/2$, e.g. between 0.8 $v_{DetMax}/2$ and 1.2 $v_{DetMax}/2$, more preferable exactly $v_D=v_{DetMax}/2$.

In order to avoid ambiguities due to the 2π periodicity of the interferometric signal, it is preferred that the plurality of SOCT spectra are acquired at time intervals shorter than $\pi/(2k_0 v_D)$. More preferably, said time intervals are chosen to be below $\pi/(2k_{Max} v_D)$.

Figure 5:
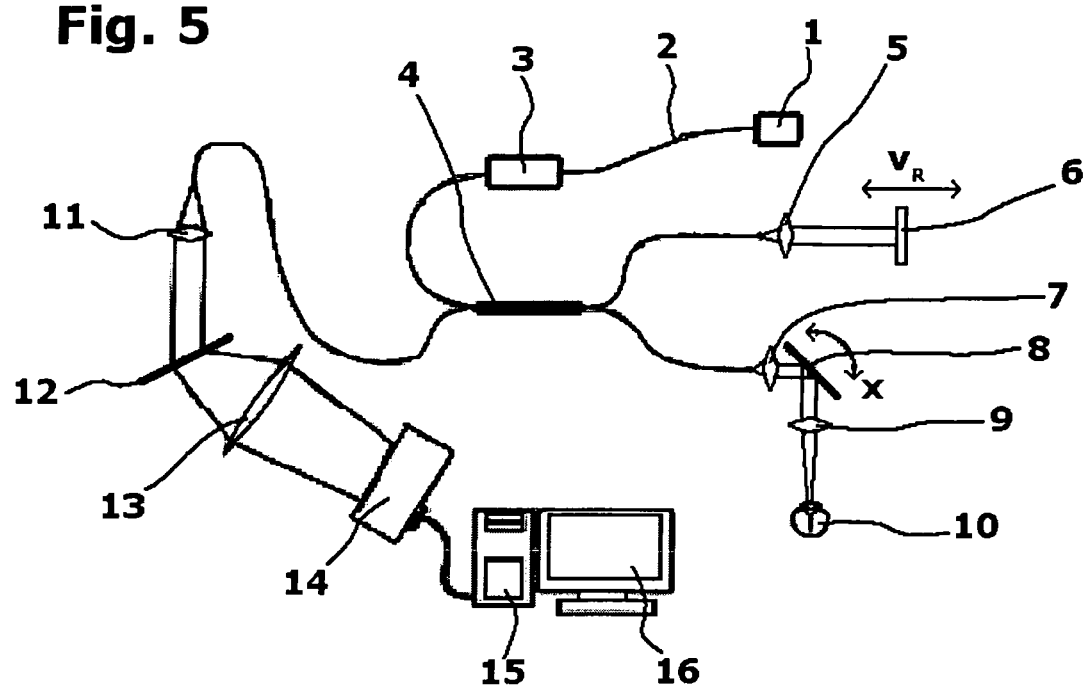
FIG. 5 is a schematic diagram of an apparatus according to the invention.

The apparatus according to the invention will now be described in greater detail with the help of an example shown in FIG. 5.

A light source 1, e.g. a superluminescent diode, emits low coherent broadband light into an optical fiber system 2. An optical isolator 3 shields the light source 1 from returning light. A fiber coupler 4 divides the light into a first portion, the reference light, and a second portion, the sample light. The reference light propagates along the reference path where it exits the optical fiber system 2 to be collimated by a collimating lens 5 and directed to a reference mirror 6. The reference mirror 6 is moved in parallel to the incident light with a velocity $v_R$. For repeated measurements, the reference mirror 6 is moved back and forth, this movement being symbolized by a left right arrow $v_R$. Where $v_R≠0$, $v_D$ may be equal to $v_R$ and spectra can be acquired. As $v_D$ should be preferably constant, the mirror should be moved with a constant speed at least in one direction and at least during a major part of this movement. If spectra shall be acquired during the movements of the mirror in both directions, the change of algebraic sign must be accounted for in the evaluation.

The sample light exits from the optical fiber system 2, too, and is collimated by a collimating lens 7. The collimated light is reflected by a scanning mirror 8. The scanning mirror 8 is pivoted about an axis to scan along the x axis, which movement is symbolized by the curved arrow x. A focusing lens 9 focuses the sample light on a sample 10. If, as shown in this example, said sample 10 is an eye and the region under investigation is a part of the retina, the eye lens may be used for further focusing on the region of interest. From here, the sample light returns along the sample path back to the fiber coupler 4, which recombines the sample light with the returning reference light.

One portion of the recombined light exits the fiber coupler 4 through the port connected to the light source 1, but it is blocked by optical isolator 3. The other portion passes through the remaining port to exit the optical fiber system 2 and to be spectrally analyzed by a spectrometer. The essential elements of the spectrometer are a collimating optics 11, a grating 12, a focusing optics 13 and a line sensor 14. The collimating optics 11 directs the light to the grating 12 which decomposes it into its spectral components. Each component is focused by focusing optics 13 onto a sensor pixel of the line sensor 14. Each sensor pixel converts the intensity of the incident light into an electric signal. These signals are read out by a computer 15, which is connected to the line sensor 14. The computer 15 is arranged for triggering the recordings of data sets I(k, t). It triggers the recordings during the periods of time in which $v_R=v_D$.

Furthermore, the computer 15 comprises a timing unit arranged for triggering said recordings in time intervals shorter than $\pi/(2k_0 v_D)$, more preferably shorter than $\pi/(2k_{Max} v_D)$. The time intervals are preferably adjustable to constant values $\Delta t$.

The computer 15 further comprises a computation unit arranged for transforming said data set $I(k, t)$ to a data set $I(k, v)$ and further do a data set $I(z, v)$, where z represents the positions of back-scattering structures of the sample along the axis of the incident light and v represents the velocity component along said axis of back-scattering structures of the sample. The computation unit is preferably arranged for performing said $I(k, v)$ to $I(z, v)$ transformation only for a portion of the data set $I(k, v)$ for which v is beyond a certain value. This mode of operation allows for further processing only the data for the real image so that computation resources are saved.

The illustrated SOCT setup has a range of detectable velocities v which range is 0 to $v_{DetMax}$. If the timing unit triggers data acquisitions at constant time intervals $\Delta t$, $v_{DetMax}$ will be $\pi/(2k_0\Delta t)$ or, if the influence of different wavelengths shall be accounted for, $\pi/(2k_{Max}\Delta t)$, where $k_0$ is the central wavenumber and $k_{Max}$ is the maximum wavenumber of the spectrum used for the measurement. As in most applications, the distribution of velocities will be centered around v=0, it is advisable to shift this center with the imposed Doppler shift to the center of detectable velocities, i.e. to $v_{DetMax}/2$. It is therefore advantageous to select $v_D$ around $v_{DetMax}/2$, e.g. between 0.4 $v_{DetMax}/2$ and 0.6 $v_{DetMax}/2$, more preferably exactly $v_D=v_{DetMax}/2$. These considerations do not only apply to the illustrated apparatus, but to apparatus according to the invention in general.

The results, i.e. the measured image and velocity distribution data, may be visualized on a display 16.

The computer 15 may be a standard personal computer or a special device. It may also be integrated with the spectrometer into one single device.

The invention claimed is:

1. Method for measuring the spatial and velocity distribution of scattering structures of a sample of semitransparent matter comprising the steps of
    acquiring sequentially a plurality of spectral optical coherence tomography spectra $I(k)$ comprising data belonging to a real image and data belonging to a mirror image, for which time intervals between two recordings are known so that a data set $I(k, t)$ representing the time dependence of the recorded spectra is generated,
    transforming said data set $I(k, t)$ to a data set $I(z, v)$ by performing a k-z transformation and a t-v transformation, where z represents the positions of back-scattering structures of the sample along the axis of the incident light and v represents the velocity component along said the axis of back-scattering structures of the sample,
    the method comprising:
    selecting a velocity $v_D$ such that, after said t-v transformation, the range for v for all data belonging to the real image does not overlap with the range for v for all data belonging to the mirror image, wherein $v_{Min} \le v_D < v_{DetMax}$ wherein $v_{Min}$ is the minimum velocity producing a detectable phase difference between the data belonging to the real image and the data belonging to the mirror image and wherein for a time interval $\Delta t$ between recordings of the spectra $I(k)$, the maximum velocity $v_{DetMax}$ is $\pi/(2k_0\Delta t)$, where $k_0$ is the central wavenumber, or maximum velocity $v_{DetMax}$ is $\pi(2k_{Max}\Delta t)$, where $k_{max}$ is the maximum wave number of the spectrum used for the measurement,
    imposing a Doppler shift on a light, whereby a sample light and a reference light used in the method appear at a point of recombination as originating from sources moving relatively to each other with the selected velocity $v_D$, characterized in that the Doppler shift is imposed by reflecting the light with a mirror moving with a velocity component $v_D$ along the axis of the reflected light.

2. Method according to claim 1, characterized in that said Doppler shift is imposed on the reference light.

3. Method according to claim 1, characterized in that said time intervals are shorter than $\pi/(2k_o v_D)$.

4. Method according to claim 3, characterized in that said time intervals are shorter than $\pi/(2k_{max} v_D)$.

5. Method according to claim 1, characterized in that the t-v transformation is performed first and that the k-z transformation is performed only for a portion of the data set $I(k, v)$ for which v is beyond a certain value.

6. Apparatus for measuring the spatial and velocity distribution of scattering structures of a sample of semi-transparent matter comprising an arrangement for spectral optical coherence tomography comprising a sample path and a reference path, wherein said arrangement is configured to record spectra sequentially after known time intervals so that a data set $I(k, t)$ representing the time dependence of the recorded spectra may be generated, said recorded spectra comprising data belonging to a real image and data belonging to a mirror image,
    characterized in that, for a velocity $v_D$ selected such that, after said t-v transformation, the range for v for all data belonging to the real image does not overlap with the range for v for all data belonging to the mirror image, wherein $v_{Min} \le v_D < v_{DetMax}$, wherein $v_{Min}$ is the minimum velocity producing a detectable chase difference between the data belonging to the real image and the data belonging to the mirror image and wherein for a time interval $\Delta t$ between recordings of the spectra $I(k)$, the maximum velocity $v_{DetMax}$ is $\pi/(2k_0\Delta t)$, where $k_0$ is the central wavenumber, or maximum velocity $v_{DetMax}$ is $\pi/(2k_{Max}\Delta t)$, where $k_{Max}$ is the maximum wave number of the spectrum used for the measurement,
    the apparatus further comprises means for imposing a Doppler shift on the light so that light in the sample path and light in the reference path appear at the point of recombination as originating from sources moving relatively to each other with the selected velocity $v_D$.

7. Apparatus according to claim 6, characterized in that said means for imposing a Doppler shift is placed in the reference path.

8. Apparatus according to claims 6 or claim 7, characterized in that said means for imposing a Doppler shift comprises a moving mirror.

9. Apparatus according to claim 6, characterized in that said apparatus further comprises a timing unit arranged for adjusting said time intervals to be shorter than $\pi/(2k_o v_D)$.

10. Apparatus according to claim 9, characterized in that said apparatus further comprises a timing unit arranged for adjusting said time intervals to be shorter than $\pi/(2k_{Max} v_D)$.

11. Apparatus according to claim 6, characterized in that said apparatus further comprises a computation unit arranged for transforming said data set $I(k, t)$ to a data set $I(z, v)$ by performing a k-z transformation and a t-v transformation, where z represents the positions of back-scattering structures of the sample along the axis of the incident light and v represents the velocity component along said axis of back-scattering structures of the sample.

12. Apparatus according to claim 11, characterized in that said computation unit is arranged for performing said t-v transformation first and said k-z transformation only for a portion of the data set I(k, v) for which v is beyond a certain value.

13. Method for measuring the spatial and velocity distribution of scattering structures of a sample of semitransparent matter comprising the steps of
    acquiring sequentially a plurality of spectral optical coherence tomography spectra I(k),
    for which the time intervals between two recordings are known so that a data set I(k, t) representing the time dependence of the recorded spectra is generated,
    transforming said data set I(k, t) to a data set I(z, v) by performing a k-z transformation and a t-v transformation, where z represents the positions of back-scattering structures of the sample along the axis of the incident light and v represents the velocity component along said axis of back-scattering structures of the sample, characterized in that the t-v transformation is performed first and that the k-z transformation is performed only for a portion of the data set I(k, v) for which v is beyond a certain value,
    selecting a velocity $v_D$ such that, after said t-v transformation, the range for v for all data belonging to the real image does not overlap with the range for v for all data belonging to the mirror image, wherein $v_{Min} \leq v_D < v_{DetMax}$, wherein $v_{Min}$ is the minimum velocity producing a detectable phase difference between the data belonging to the real image and the data belonging to the mirror image and wherein for a time interval $\Delta t$ between recordings of the spectra I(k), the maximum velocity $v_{DetMax}$ is $\pi/(2k_0\Delta t)$, where $k_0$ is the central wavenumber, or maximum velocity $v_{DetMax}$ $\pi/(2k \Delta t)$ where $k_0$ is the maximum wave number of the spectrum used for the measurement, and
    imposing a Doppler shift on the light, whereby the sample light and the reference light used in the method appear at the point of recombination as originating from sources moving relatively to each other with the selected velocity $v_D$, characterized in that the Doppler shift is imposed by reflecting the light with a mirror moving with a velocity component $v_D$ along the axis of the reflected light.

14. Apparatus for measuring the spatial and velocity distribution of scattering structures of a sample of semi-transparent matter comprising an arrangement for spectral optical coherence tomography comprising a sample path and a reference path, wherein said arrangement is configured to record spectra sequentially after known time intervals $\Delta t$ so that a data set I(k, t) representing the time dependence of the recorded spectra may be generated,
    characterized in that, for a velocity $v_D$ selected such that, after said t-v transformation, the range for v for all data belonging to the real image does not overlap with the range for v for all data belonging to the mirror image, wherein $v_{Min} \leq v_D < v_{DetMax}$, wherein $v_{Min}$ is the minimum velocity producing a detectable chase difference between the data belonging to the real image and the data belonging to the mirror image and wherein for a time interval $\Delta t$ between recordings of the spectra I(k), the maximum velocity $v_{DetMax}$ is $\pi/(2k_0\Delta t)$, where $k_0$ is the central wavenumber, or maximum velocity $v_{DetMax}$ is $\pi/(2k_{Max}\Delta t)$, where $k_{Max}$ is the maximum wave number of the spectrum used for the measurement, the apparatus further comprises means for imposing a Doppler shift on the light so that light in the sample path and light in the reference path appear at the point of recombination as originating from sources moving relatively to each other with the selected velocity $v_D$,
    and characterized in that said apparatus further comprises a computation unit arranged for transforming said data set I(k, t) to a data set I(z, v) by performing a k-z transformation and a t-v transformation, where z represents the positions of back-scattering structures of the sample along the axis of the incident light and v represents the velocity component along said axis of back-scattering structures of the sample,
    characterized in that said computation unit is arranged for performing said t-v transformation first and said k-z transformation only for a portion of the data set I(k, v) for which v is beyond a certain value.

* * * * *